(12) United States Patent
Rubin et al.

(10) Patent No.: US 11,980,352 B2
(45) Date of Patent: May 14, 2024

(54) NASAL IRRIGATION DIAGNOSTIC ASSEMBLY

(71) Applicant: Preva, LLC, Weston, FL (US)

(72) Inventors: Keith Rubin, Ft. Lauderdale, FL (US); Ken Solovay, Weston, FL (US); James Layer, Cooper City, FL (US); Alfred A. Desimone, Ft. Lauderdale, FL (US); Bin Yan, Miami, FL (US)

(73) Assignee: PREVA, LLC, Weston, FL (US)

( * ) Notice: Subject to any disclaimer, the term of this patent is extended or adjusted under 35 U.S.C. 154(b) by 0 days.

(21) Appl. No.: 17/888,396

(22) Filed: Aug. 15, 2022

(65) Prior Publication Data

US 2023/0032349 A1   Feb. 2, 2023

Related U.S. Application Data

(63) Continuation of application No. 16/796,545, filed on Feb. 20, 2020, now abandoned, which is a
(Continued)

(51) Int. Cl.
*A61B 10/00* (2006.01)
*A61B 5/00* (2006.01)
(Continued)

(52) U.S. Cl.
CPC .......... *A61B 10/0045* (2013.01); *A61B 5/145* (2013.01); *A61B 5/14507* (2013.01);
(Continued)

(58) Field of Classification Search
CPC . A61B 10/0045; A61B 5/145; A61B 5/14507; A61B 5/1468; A61B 5/6819;
(Continued)

(56) References Cited

U.S. PATENT DOCUMENTS

| 2,566,806 A | 9/1951 | Miller |
| 3,429,313 A | 2/1969 | Romanelli |

(Continued)

FOREIGN PATENT DOCUMENTS

| CA | 2976418 | 6/2022 |
| CH | 691885 | 11/2001 |

(Continued)

OTHER PUBLICATIONS

Carrasquilla, et al, Chemistry a European Journal Communication, Patterned Paper Sensors Printed with Long-Chain DNA Aptamers, 21, 7369-7373, Wiley Online Library, Mar. 27, 2015.

(Continued)

*Primary Examiner* — Benjamin R Whatley
*Assistant Examiner* — Jacqueline Brazin
(74) *Attorney, Agent, or Firm* — MALLOY & MALLOY, PL (57) ABSTRACT

A nasal irrigation diagnostic assembly comprising an irrigation device including a fluid collection portion structured to retain a biological sample, in the form of waste solution from the nasal cavity resulting from irrigation. A detection member disposed on said irrigation device is exposed to the biological sample and is structured to determine the existence of at least one analyte within the biological sample of the waste solution. The detection member comprises a plurality of detection zones individually structured to analyze the biological sample upon engagement therewith, wherein said plurality of zones include at least a reaction zone and a detection zone, which respectively include reagents cooperatively and collectively formulated to detect the existence of the at least one analyte within biological sample of the waste solution. A control zone may also be included to indicate the intended operability of at least the detection member.

7 Claims, 3 Drawing Sheets

Related U.S. Application Data continuation-in-part of application No. 16/688,654, filed on Nov. 19, 2019, now Pat. No. 11,179,513, and a continuation of application No. 15/604,205, filed on May 24, 2017, now abandoned, which is a continuation-in-part of application No. 15/299,792, filed on Oct. 21, 2016, now abandoned, said application No. 16/688,654 is a continuation-in-part of application No. 15/257,409, filed on Sep. 6, 2016, now Pat. No. 10,478,547, which is a continuation-in-part of application No. 13/664,034, filed on Oct. 30, 2012, now Pat. No. 9,433,724.

(60) Provisional application No. 62/244,362, filed on Oct. 21, 2015.

(51) Int. Cl.
*A61B 5/145* (2006.01)
*A61B 5/1468* (2006.01)
*A61M 3/02* (2006.01)
*G01N 33/487* (2006.01)
*G01N 33/543* (2006.01)
*G01N 33/558* (2006.01)
*G01N 33/569* (2006.01)

(52) U.S. Cl.
CPC .......... *A61B 5/1468* (2013.01); *A61B 5/6819* (2013.01); *A61M 3/02* (2013.01); *A61M 3/0212* (2014.02); *G01N 33/4875* (2013.01); *G01N 33/54353* (2013.01); *G01N 33/558* (2013.01); *G01N 33/569* (2013.01); *G01N 33/56911* (2013.01); *A61M 2210/0618* (2013.01); *G01N 2333/235* (2013.01); *G01N 2469/10* (2013.01)

(58) Field of Classification Search
CPC .................. A61M 3/02; A61M 3/0212; A61M 2210/0618; G01N 33/4875; G01N 33/54353; G01N 33/558; G01N 33/569; G01N 33/56911; G01N 2333/235; G01N 2469/10
USPC ........................................................ 600/563
See application file for complete search history.

(56) References Cited

U.S. PATENT DOCUMENTS

| | | | |
|---|---|---|---|
| 4,294,251 A | 10/1981 | Greenwald et al. | |
| 4,457,747 A | 7/1984 | Tu | |
| 4,655,197 A | 4/1987 | Atkinson | |
| 4,663,628 A | 5/1987 | Duncan et al. | |
| 4,790,979 A * | 12/1988 | Terminiello .......... | B01L 3/5023 600/583 |
| 4,904,238 A | 2/1990 | Williams | |
| 4,924,862 A | 5/1990 | Levinson | |
| 4,998,915 A | 3/1991 | Hannah | |
| 5,009,634 A | 4/1991 | Feldman et al. | |
| 5,277,175 A | 1/1994 | Riggs et al. | |
| 5,505,193 A | 4/1996 | Ballini et al. | |
| 5,542,918 A | 8/1996 | Atkinson | |
| 5,649,530 A | 7/1997 | Ballini | |
| 6,022,748 A | 2/2000 | Charych et al. | |
| 6,135,358 A | 10/2000 | Ballini | |
| 6,145,703 A | 11/2000 | Opperman | |
| 6,736,792 B1 | 5/2004 | Liu | |
| 6,907,879 B2 | 6/2005 | Drinan et al. | |
| 7,063,686 B2 | 6/2006 | Mezzoli | |
| 7,080,980 B2 | 7/2006 | Klupt | |
| 7,143,763 B2 | 12/2006 | Abate | |
| 7,569,031 B2 | 8/2009 | Britto | |
| 7,959,597 B2 | 6/2011 | Baker et al. | |
| 7,981,077 B2 | 7/2011 | Hoke et al. | |
| 8,048,023 B2 | 11/2011 | Hoke et al. | |
| 8,343,114 B2 | 1/2013 | Mehta | |
| 9,289,547 B2 | 3/2016 | Layer et al. | |
| 9,433,724 B2 | 9/2016 | Rubin et al. | |
| 10,265,462 B2 | 4/2019 | Layer et al. | |
| 10,478,547 B2 | 11/2019 | Rubin et al. | |
| 11,311,706 B2 | 4/2022 | Layer et al. | |
| 2003/0069549 A1 | 4/2003 | MacMahon et al. | |
| 2003/0089367 A1 | 5/2003 | Abate | |
| 2003/0158527 A1 | 8/2003 | Mezzoli | |
| 2003/0172925 A1 | 9/2003 | Zocca et al. | |
| 2004/0182388 A1 | 9/2004 | Djupesland | |
| 2005/0004498 A1 | 1/2005 | Klupt | |
| 2005/0011282 A1 | 1/2005 | Voege et al. | |
| 2007/0149922 A1 | 6/2007 | Schneider et al. | |
| 2008/0138842 A1 | 6/2008 | Boehringer et al. | |
| 2008/0154183 A1 | 6/2008 | Baker et al. | |
| 2008/0183128 A1 | 7/2008 | Morriss et al. | |
| 2008/0221507 A1 | 9/2008 | Hoke et al. | |
| 2008/0312674 A1 | 12/2008 | Chen et al. | |
| 2009/0104690 A1 | 4/2009 | Bayliff et al. | |
| 2009/0197283 A1 * | 8/2009 | Gold ..................... | B01L 3/5029 435/7.9 |
| 2009/0281483 A1 | 11/2009 | Baker et al. | |
| 2009/0281485 A1 | 11/2009 | Baker et al. | |
| 2010/0016787 A1 | 1/2010 | Shapiro et al. | |
| 2010/0152653 A1 | 6/2010 | Hoke et al. | |
| 2010/0154653 A1 | 6/2010 | Douglas et al. | |
| 2011/0132369 A1 | 6/2011 | Sanchez | |
| 2011/0144588 A1 | 6/2011 | Taylor et al. | |
| 2011/0220119 A1 | 9/2011 | Lowenstein et al. | |
| 2012/0135437 A1 * | 5/2012 | Brennan ................ | B05D 7/584 435/287.9 |
| 2012/0179118 A1 | 7/2012 | Hair | |
| 2013/0012869 A1 | 1/2013 | Cha et al. | |
| 2013/0137598 A1 * | 5/2013 | Verschoor .......... | G01N 33/5695 435/7.92 |
| 2013/0244314 A1 | 9/2013 | Yuki et al. | |
| 2014/0121592 A1 * | 5/2014 | Rubin ..................... | A61M 1/77 604/35 |
| 2014/0193925 A1 * | 7/2014 | Bhattacharyya .......................... | G01N 33/54366 422/69 |
| 2014/0200507 A1 | 7/2014 | Azeez | |
| 2014/0275857 A1 | 9/2014 | Toth et al. | |
| 2014/0371690 A1 | 12/2014 | Sprada et al. | |
| 2015/0118689 A1 * | 4/2015 | Egan ..................... | A61B 5/7203 435/7.1 |
| 2016/0054310 A1 | 2/2016 | Brennan et al. | |
| 2016/0303308 A1 | 10/2016 | Layer et al. | |
| 2016/0375192 A1 | 12/2016 | Rubin et al. | |
| 2019/0314621 A1 | 10/2019 | Layer et al. | |
| 2020/0188575 A1 | 6/2020 | Rubin et al. | |
| 2020/0297915 A1 | 9/2020 | Rubin et al. | |

FOREIGN PATENT DOCUMENTS

| | | |
|---|---|---|
| EP | 197778 | 8/2008 |
| EP | 2389918 | 11/2011 |
| EP | 2914312 | 8/2017 |
| JP | 2010520033 | 6/2010 |
| JP | 2010527636 | 8/2010 |
| JP | 2016-515410 | 5/2016 |
| WO | WO2008058160 | 5/2008 |
| WO | WO2008109726 | 9/2008 |
| WO | WO2010126586 | 11/2010 |
| WO | WO2011127407 | 10/2011 |
| WO | WO2014070854 | 5/2014 |
| WO | WO2015123276 | 8/2015 |

OTHER PUBLICATIONS

Liu et al., Angewandte Chemie, Target-Induced and Equipment-Free DNA Amplification With a Simple Paper Device, 128, 2759-2763, Wiley Online Library, Jan. 8, 2016.

(56) References Cited

OTHER PUBLICATIONS

Translation EP-238918-A1, EPO Patent Translate, dated Mar. 2, 2019.

\* cited by examiner

NASAL IRRIGATION DIAGNOSTIC ASSEMBLY

CLAIM OF PRIORITY

The present application is a continuation application of previously filed U.S. patent application Ser. No. 16/796,545 filed on Feb. 20, 2020, which is a continuation of U.S. patent application Ser. No. 15/604,205 filed on May 24, 2017, which is a continuation-in-part application of U.S. patent application Ser. No. 15/299,792 filed on Oct. 21, 2016, which claims priority to provisional patent application having U.S. Ser. No. 62/244,362 filed on Oct. 21, 2015. This present application is also a continuation-in-part application of previously filed U.S. patent application Ser. No. 16/688,654 filed on Nov. 19, 2019, which is a continuation-in-part application of U.S. patent application Ser. No. 15/257,409 filed on Sep. 6, 2016, which matured into U.S. Pat. No. 10,478,547 on Nov. 19, 2019, which is also a continuation-in-part application of U.S. patent application Ser. No. 13/664,034 filed on Oct. 30, 2012, which matured into U.S. Pat. No. 9,433,724 on Sep. 6, 2016. The contents of each of the above are incorporated herein in their entirety by reference.

BACKGROUND OF THE INVENTION

Field of the Invention

This invention relates to a nasal irrigation diagnostic assembly including a nasal irrigation device structured to clean the nasal cavity and collect and retain waste solution from the nasal cavity resulting from the irrigation. A detector member disposed on the irrigation device includes a plurality of detection zones which are structured to analyze a biological sample defined by the waste solution. The plurality of detection zones include reagents cooperatively formulated to detect the existence of at least one analyte and associated pathogens/pathogen specific proteins within the waste solution/biological sample.

Description of the Related Art

Poor nasal hygiene is a common problem existing and prevalent in individuals of all ages and can lead to nasal and sinus disease. Such disease, including congestion, infection, and other pathologic conditions of the nasal passages and paranasal sinuses, is typically caused by viruses, bacteria and other microbes and/or exposure to environmental allergens. Sino-nasal disease is one of the most common medical conditions in the United States, afflicting approximately 33 million people and accounting for over $5.8 billion in healthcare costs annually ("Nasal Congestion: More than physical obstruction," Science Daily, Oct. 17, 2011). Nasal congestion and the associated feeling of obstruction is the symptom that typically causes individuals to seek medical assistance. Common signs and symptoms arising from poor nasal hygiene include nasal inflammation, rhinorrhea, sinusitis, irritation, pain and nasal passage blockage. Medications used to treat nasal pathology inherently include potential side effects and possibly excessive costs.

A number of studies demonstrate that regular use of nasal irrigation is an effective therapy in the relief of symptoms associated with poor nasal hygiene (e.g. Rabago et.al, Journal of Family Practice. 2002; 51(12):1049-1055; Tomooka et.al, Laryngoscope. 2000 July; 110(7):1189-93.) Other similarly related clinical studies indicate that nasal wash with isotonic saline can improve certain infection outcomes (Slapak et.al, Archives of Otolaryngology-Head & Neck Surgery. 2008; January; 134(1):67-74) and that regular nasal irrigation is a beneficial therapy for the treatment of allergy related symptoms (e.g. Garavello et.al, Pediatr Allergy Immunol. 2003 April; 14(2):140-3.) Accordingly, these studies indicate that nasal irrigation is a clinically proven method of improving sinus related disease, including allergies and infections. Current standards of care for nasal irrigation involves exposing the nasal cavity and passages to a streaming volume of saline or other prophylactic or therapeutic solutions.

In addition to cleansing the nasal cavities of pathogens and allergens, such irrigation related treatment is also believed to include a number of physiological effects. These include stimulation of mucosal cilia and increasing physiologic flow of mucous, which individually or in concert may reduce the risk of nasopharyngeal and sinus localization of pathogens and allergens, thereby reducing potential morbidity and mortality. Further, irrigation therapy that includes rinsing of the interior of the nasal cavity, typically washes away waste, microbial by-products, and/or encrustations, which may be the causal factor in a number of undesirable conditions and symptoms. Conventional irrigation techniques are intended to keep sinus cavities, nasal passages, and the drainage from sinuses to nasal passage in a healthy state. Improving nasal hygiene with irrigation thus reduces the likelihood that the nasal cavity, paranasal sinuses, and related structures will become colonized with pathogens, thereby reducing the potential for morbidity and mortality.

As conventionally practiced, nasal irrigation is known to apply and utilize various types of manually or automatically operated irrigation and/or nasal aspirators. As such, irrigating fluid is applied in a manner or in such volume sufficient to flood the nasal cavity in an attempt to remove the aforementioned pathogens, allergens, encrustations, or waste after the application of the irrigating fluid has been completed. However, disadvantages at least partially associated with the flooding of the nasal cavity, occur when the irrigating and aspirating steps are conducted separately or successively, which can lead to suboptimal cleansing and disinfection. As typically operated, existing manual devices serve to sequentially, rather than simultaneously, deliver irrigation agent to the nasal cavity followed by a subsequent and frequently delayed aspiration of the agent and accumulated waste.

However, conventional and/or known irrigation devices are almost exclusively directed to the irrigation procedure per se. As such, such conventional devices do not have the ability or intent to perform any type of diagnostic procedure for the purpose of detecting infectious bacterial or viral matter.

Accordingly, there is a need in this art for a nasal irrigation diagnostic assembly which is operable to detect various types of infectious diseases and which could have multiple indicators for different/multiple infection diseases. Further, specific compounds can be added to an irrigation solution so as to facilitate clearance of nasal contaminants. Moreover, multiple bacteria or viral contaminants could be screened. Also, such a preferred and proposed assembly should be operable to detect allergens that accumulate within the nasal cavity by breathing in substances to which an individual may be commonly exposed. Also, a proposed nasal irrigation diagnostic assembly, in one or more preferred embodiments, should be able to diagnose and potentially eliminate specific bacteria from the nasal cavity including, but not limited to, *Staphylococcus aureus*, the main causal agent of hospital acquired infections which often originate in the nasal cavity of a patient undergoing surgery. Eliminating *S. Aureus* from the nasal cavity has shown to decrease the number of hospital acquired postoperative infection.

SUMMARY OF THE INVENTION

The present invention is directed to a nasal irrigation diagnostic assembly, which in use provides for effective infectious disease detection through the analysis of a biological sample, in the form of aspirate or waste solution resulting from irrigation of the nasal cavity. The waste solution/biological sample is retrieved and retained by the nasal irrigation device from the nasopharyngeal cavity for analysis.

Moreover, the detection assembly of the present invention accomplishes the cleaning of the nasal cavity of particulate, bacterial and viral matter and can be easily, comfortably and efficiently used by non-medical individuals. In use the diagnostic assembly of the present invention serves to detect one or more analyte species with high sensitivity and with specificity in a nasal waste solution/biological sample and generating reliable data within a comparatively short time. Finally, the detection assembly may be disposed of after use by being constructed from low-cost, disposable components.

Accordingly, one or more preferred embodiments of the nasal irrigation diagnostic assembly of the present invention, is provided in the form of a hand held nasal irrigation device having a reservoir capable of at least initially holding cleaning solutions in volumes, preferably in the range of 10-25 cc. By way of example nasal irrigation devices of the type disclosed in U.S. Pat. Nos. 9,289,547 and 9,433,724, issued to the inventors herein, may be used in the practice of the nasal irrigation diagnostic assembly of the present invention. However, as will be described and clarified herein, the structural and operative features of the included nasal irrigation device may differ from those disclosed in the above noted patent collection. However, in at least one embodiment of the present invention the nasal irrigation device utilized should include a portion, area or chamber for collecting the waste solution from the nasal cavity, retrieved as a result of the irrigation/cleaning procedure applied by the nasal irrigation device.

More specifically, the included nasal irrigation device preferably directs cleaning fluid into the naval cavity while substantially concurrently retrieving and collecting the waste fluid within the aforementioned collection portion of the nasal irrigation device. As a result, the waste solution that drains back into the collection portion of the nasal irrigation device contains waste material retrieved from the nasal cavity, which may be at least partially in the form of particulate matter. A preferred cleaning procedure may also result in continuous contact of the epithelium with the fresh cleaning solution initially applied by the irrigation device, therefore greatly enhancing the cleaning efficiency of the nasal cavity. Therefore, as indicated the collected waste solution is used as a biological sample. This differs from conventional procedures wherein a nasopharyngeal swab is applied to the nasal cavity by medical personnel.

As also explained in greater detail hereinafter, another structural and operative feature of the various preferred embodiments of the present invention is directed to the inclusion of a detection member. In practicing the included diagnostic procedure, the detection member is disposed on and/or within the nasal irrigation device and in contact with the collected waste solution. Further, the detection member is structured to facilitate fluid flow along its length or throughout predetermined portions or sections thereof. Such liquid flow may be accomplished by capillary action and in at least one preferred embodiment the detection member has a paper based material structured to facilitate such fluid flow.

Moreover, the detection member may have a substantially elongated "strip" like configuration comprising a plurality of zones or sections operative to detect pathogens and possibly signal a user that the nasal irrigation device and detection member is operable and has accomplished its intended purpose/function. Further, when in strip form, the detection member may be substantially "vertically" or otherwise appropriately oriented. In such an orientation one end of the detection member, such as a sample pad, portion, zone, etc. thereof, may be disposed in direct fluid communication with the interior of the collection portion of the nasal irrigation device. In such a disposition, the sample pad of the detection member strip will be disposed in direct contact with the waste solution once it is retrieved from the nasal cavity during the irrigation procedure and retained within the collection portion.

However, it is noted that the detection member may assume a variety of structures, configurations, sizes, etc. other than the strip-like configuration set forth above. Therefore, one operative feature of the detection member is the disposition of the plurality of indication zones, relative to one another, such that the waste solution retrieved from the nasal cavity will be successively exposed to each of the plurality of detection zones and the reagents contained in the different detection zones.

In more specific terms, the detection member contains a plurality of at least two of such zones and in one or more additional embodiments, a plurality of at least three such zones. Such detection zones preferably comprise a reaction zone (R), a detection zone (D) and possibly a control zone (C). As indicated above, the detection member may also include a sample pad, segment or section which is disposed within the collected biological sample of waste solution, retained within the nasal irrigation device or otherwise disposed in direct contact with the collected waste solution.

The reaction zone (R) includes components comprising analyte, analyte specific anti-body-chromophore conjugate, and control conjugate. As such, the reaction zone contains the analyte specific anti-body-chromophore conjugate that binds to, by way of example, a pathogen or protein associated with or excreted by a pathogen. The analyte specific conjugate is soluble i.e. it will dissolve in the nasal aspirate/waste solution sample and move with the liquid flow, via capillary action, and bind to the specific analyte in the reaction zone, if present. As indicated, the reaction zone also contains a control conjugate that generates a positive signal in the control zone, if included, as discussed in more detail hereinafter.

The detection zone (D) is a section or zone of porous material that contains an immobilized anti-body that binds and immobilizes an analyte (sit?) such as for example a pathogen or protein associated with or excreted by a pathogen. Since the analyte passed through the reaction zone prior to reaching the detection zone, the analyte will be "tagged" with an analyte specific conjugate that results in the accumulation of the conjugated chromophore on the detection zone.

The control zone is a zone or section of the porous material detection member that contains an immobilized anti-body that binds and immobilizes a control analyte such as for example protein conjugate that is totally unrelated to any of the protein matter that can be found in the nasal cavity or in the waste solution emanating therefrom. The capture of the control conjugate results in the accumulation of the conjugated chromophore on the detection zone.

As practically applied, an analyte in the biological sample, for example a specific pathogen or a pathogen specific protein, binds to the soluble analyte specific conjugate. The analyte-conjugate complex continues to flow through the detection member and passes by a second, immobilized antibody that also binds to the analyte thereby immobilizing the analyte-conjugate complex at a specific location on the detection member corresponding to a "detection line". Since all analyte-conjugate complexes are concentrated in the detection zone, a line or portion of the chromophore becomes visible at the detection line. Otherwise, the analyte specific conjugate, without analyte, could pass the detection zone and the detection line undetected. Macroscopically, if an analyte is present, the diagnostic member changes colors in a window on the nasal irrigation device which is visible to the user. This provides a clear signal, alarm or other appropriate indication as to whether a specific analyte is identified in the biological sample comprising the nasal aspirate/waste solution.

In addition, a positive control signal will be generated by the control zone to verify that the sample conditions do not interfere with antigen-anti-body interaction. The control signal is generated by an anti-body-chromophore conjugate or a protein-chromophore conjugate that is also embedded in the detection member matrix together with the analyte specific conjugate in the reaction zone. The control conjugate migrates together with the nasal aspirate/waste fluid and is captured by an immobilized antibody located in the control zone, resulting in the generation of a visible signal.

Accordingly, in at least one preferred embodiment the detection member comprises a bio sensing strip or other appropriate configuration, which may be formed from a paper-based material structurally capable of capillary flow there through. In addition, the detection member could include ink-jet printed material that deposits an enzyme or colorimetric reagents onto the paper-based detection member. Color change, defining a control signal, could be achieved by target recognition, such as when the detection member contacts the microbe or toxin of interest, by the detection member converting enzyme, anti-body to a measurable, visual, preferably color, signal. Other readout mechanisms could be incorporated, such as fluorescence and ultraviolet light. However, these latter alternatives would involve additional readers, equipment, detectors.

More specifically, one preferred embodiment of the present invention comprises disposing an ink-jet printed sol-gel material that deposits an enzyme, DNAzyme, or aptamer and colorimetric reagents onto the paper-based strip. As a result, color changes could be achieved and be apparent, upon target recognition i.e. when the paper-based strip contacts the microbe or toxin of interest, by the paper converting the enzyme, antibody or aptamer-based recognition to a measurable color signal. It is recognized that other readout mechanisms could be used such as, but not limited to, fluorescence and ultraviolet light. However, one potential disadvantage associated with these latter readout mechanisms is the possible requirement for an additional reader or piece of equipment needed and/or used to detect such additional or other readout mechanisms.

Therefore, structural and operative features of the nasal irrigation diagnostic assembly of the present invention provide to a consumer, the use of a handheld diagnostic device for detecting the presence of bacterial or viral pathogens without requiring the participation of medical personnel. Further, the detection procedure provides results that are easy to read on a timely basis. In addition, the nasal irrigation device is combined with the diagnostic member and provides a continuous rinse with clean washing or cleaning liquid while draining the "contaminated" waste solution for retention and collection and use as a biological sample, in the detection procedure associated with the present invention. Operation of the present invention thereby provides a device that has the potential to sample a broader surface area of the nasopharynx compared to a manual swab or an aspiration catheter as is conventionally used in the medical profession for related diagnostic procedures.

These and other objects, features and advantages of the present invention will become clearer when the drawings as well as the detailed description are taken into consideration.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

The invention now will be described more fully hereinafter with reference to the accompanying drawings in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The present invention is directed to a nasal irrigation diagnostic assembly, generally indicated as 10, which provides for effective infectious disease detection through the analysis of a biological sample, in the form of aspirate or waste solution, retrieved and retained by the nasal irrigation device from the nasopharyngeal cavity, as a result of the irrigation of the nasopharyngeal cavity.

Moreover, the nasal irrigation diagnostic assembly 10 of the present invention accomplishes the cleaning, through irrigation, of the nasal cavity of particulate, bacterial and viral matter and can be easily, comfortably and efficiently used by non-medical individuals. In use, the diagnostic assembly 10 serves to detect the existence of one or more analyte species, with high sensitivity and specificity, in a biological sample at least partially defined by or in the form of the nasal waste solution 12. Further, the nasal irrigation diagnostic assembly 10 is operative to generate reliable data, determinative of the existence of at least one analyte within the aspirate from the nasal cavity, within a comparatively short time.

Accordingly, one or more preferred embodiments of the nasal irrigation diagnostic assembly 10 is provided in the form of a hand held nasal irrigation device 14 having a reservoir 16 capable of at least initially holding cleaning solutions in volumes, preferably in the range of 10-25 cc. However, as will be described and clarified hereinafter the structural and operative features of the included nasal irrigation device 14 may differ from those disclosed herein. Further, the nasal irrigation diagnostic assembly 10 utilized may be disposed of after use by being constructed from low-cost, disposable components. However, in at least one embodiment of the present invention the nasal irrigation device 14 being utilized should include a collection portion or chamber 18 for collecting the waste solution 12 from the nasal cavity, which is retrieved as a result of the irrigating, cleaning procedure applied by the nasal irrigation device.

As also described in greater detail hereinafter, the nasal irrigation device 14 may include an indicator window 50 or like indicator structure which provides a visual or other appropriate detectable signal or alarm that at least one analyte has been detected within the waste solution/biological sample 12. Further, the indicator window or like structure 50 may also display an appropriate signal providing an indication that the nasal irrigation diagnostic assembly 10 is operating correctly and in an intended manner.

More specifically, the included nasal irrigation device 14 preferably directs cleaning fluid into the naval cavity while substantially concurrently retrieving and collecting the waste fluid 12 within the aforementioned collection portion 18 or chamber of the nasal irrigation device 14. As a result, the waste solution 12 that drains back into the collection portion 18 of the nasal irrigation device 14 may contain waste material including, but not limited to, particulate and/or bacterial and viral matter retrieved from the nasal cavity. As such, the retrieved and at least temporarily retained waste solution 12 comprises a biological sample which will be being analyzed for the purpose of determining the existence of one or more analytes comprising a pathogen and/or pathogen specific protein. As indicated the collected waste solution 12 is used as the biological sample being analyzed, which differs from conventional procedures, wherein a nasopharyngeal swab may be applied to the nasal cavity by a medical professional.

Figure 1:
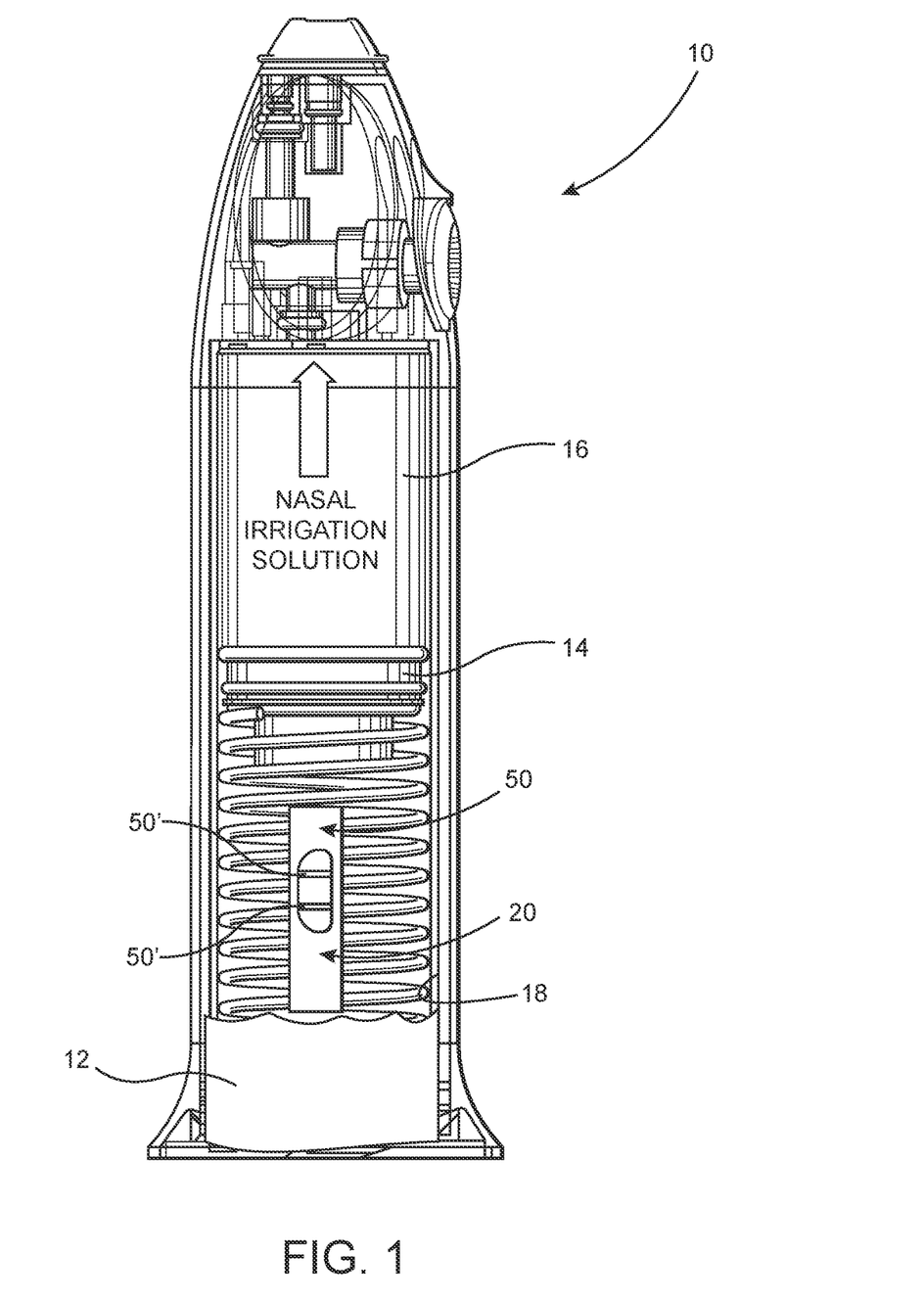
FIG. 1 is an interior view of a nasal irrigation device in at least partially schematic form and is intended to be representative of other nasal irrigation devices which may be used to implement the nasal irrigation diagnostic assembly of the present invention.
Figure 2:
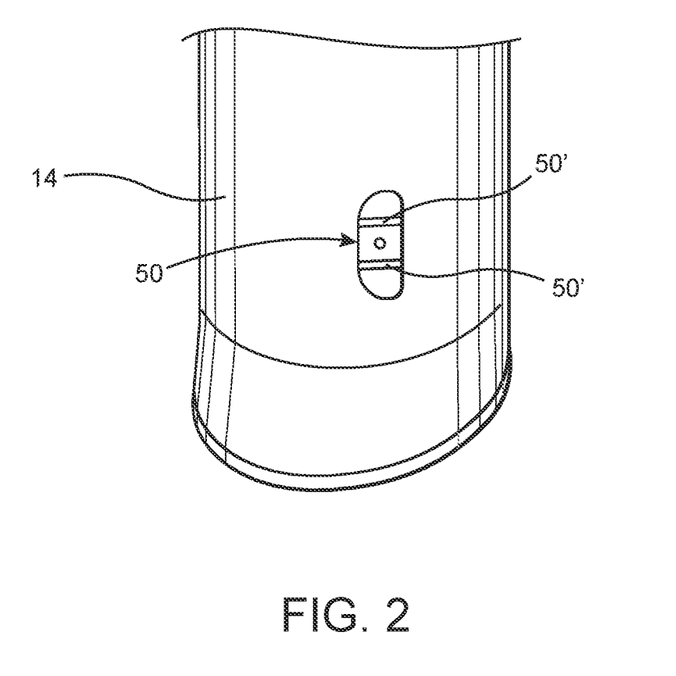
FIG. 2 is a perspective view in partial cutaway of an exterior portion of a nasal irrigation device of the type represented in FIG. 1, disclosing an indicator window or like structure.

Another structural and operative feature of the various preferred embodiments of the present invention is directed to the inclusion of a detection member 20. FIG. 1 represents the detection member 20 being mounted on the nasal irrigation device 14 in an operative position. Such an operative position includes at least a sample portion 28 of the detection member 20 being disposed within or in direct contact with the collection portion 18 and therefore in direct fluid communication and engagement with the waste solution/biological sample 12, when it is retained within the collection portion 18.

Accordingly, in practicing or applying an appropriate diagnostic procedure, the detection member 20 is disposed in contact with the collected waste solution/biological sample 12 and is structured to facilitate fluid flow along its length or throughout a plurality of detection zones included as a part of the detection member 20 as explained in greater detail with primary reference to FIGS. 3A-3D. Such liquid flow may be accomplished by capillary action and in at least one preferred embodiment the detection member 20 is at least partially formed from a paper based material to facilitate such capillary action or other fluid flow. Moreover, the paper-based material may be cellulose or nitrocellulose or a structural and operational equivalent and can be functionally printed with a controlled pattern of liquids or dies such as an ink including particles dispersed in an organic solvent. Further, the bio-ink can be composed of enzymes, aptamers, DNAzymes and/or antibodies. Printing methods may include laser treatment, plasma treatment, photolithographic, flexographic printing, screen printing, wax printing, inkjet etching, or ink jet printing.

Moreover, as represented throughout the Figures, the detection member 20 may have, but is not limited to, a substantially elongated "strip" like configuration comprising a plurality of detection zones individually and collectively operative to detect the existence of at least one analyte and associated pathogens/pathogen specific protein associated therewith. The plurality of detection zones may also include a zone cooperatively structured with other of the plurality of detection zones that signal a user that the nasal irrigation diagnostic assembly 10, including the nasal irrigation device 12 and the detection member 20 are operable to accomplish the intended diagnostic procedure. However, it is emphasized that the detection member 20 may assume a variety of structures, configurations, sizes, etc. other than the strip-like configuration set forth above and disclosed in the accompanying Figures. In addition, one operative feature of the detection member 20 is the disposition of the plurality of detection zones relative to one another, such that the waste fluid/biological sample 12 retrieved from the nasal cavity will be successively exposed to the detection zones and the reagents contained therein.

In more specific terms, the detection member 20 contains a plurality of at least two zones and in one or more additional embodiments a plurality of at least three zones. Such detection zones preferably comprise a reaction zone (R) 22, a detection zone (D) 24 and possibly a control zone (C) 26. In addition, the detection member may also include a sample segment, pad or section 28 which may be operatively disposed within the collection portion 18 or otherwise in direct engagement with the collected waste solution/biological sample 12, when retained within the nasal irrigation device 14. While the structure, configuration and overall operation of the nasal irrigation device 14 may vary from that represented in the embodiment of FIG. 1, the detection member 20, and preferably the sample segment 28 will be in direct contact with the collected waste solution/biological sample 12 upon it being collected and retained within the irrigation device 14. Further, an absorption pad 30 may also be included in the detection member 20 and may be structured to facilitate the fluid flow, such as by means of capillary action as also represented throughout FIGS. 3A-3D.

Figure 3A:
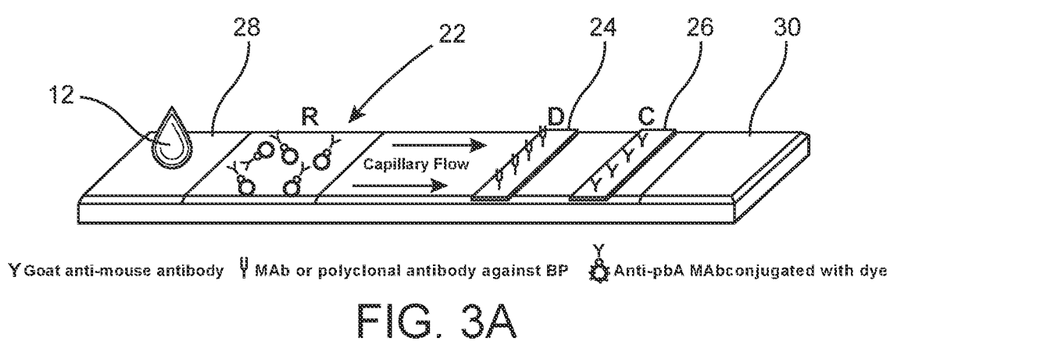
FIG. 3A is a schematic representation of a detection member and accompanying legend of the type utilized in the assembly of the present invention.
Figure 3B:
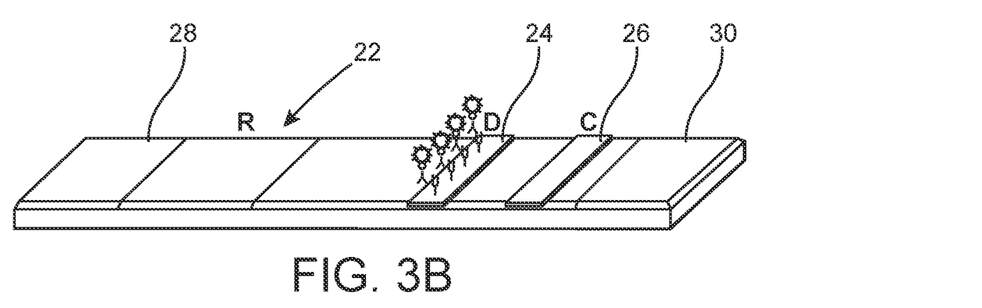
FIG. 3B is a schematic representation of the detection member in FIG. 3A representing operative features of one of a plurality of detection zones associated with the detection member.
Figure 3C:
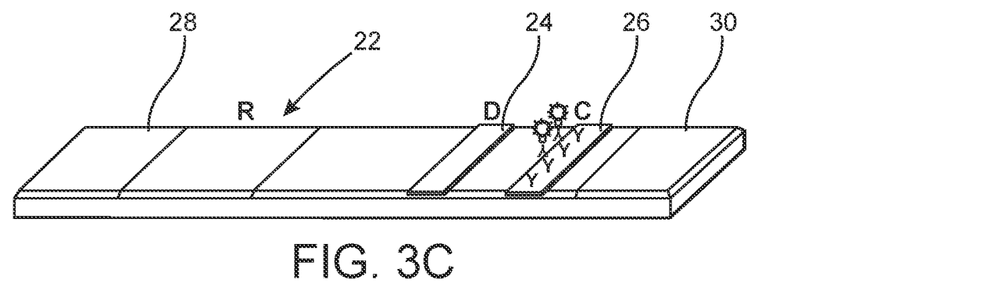
FIG. 3C is a schematic representation of the detection member of FIGS. 3A and 3B representing operative features of another one of a plurality of detection zones associated with the detection member.
Figure 3D:
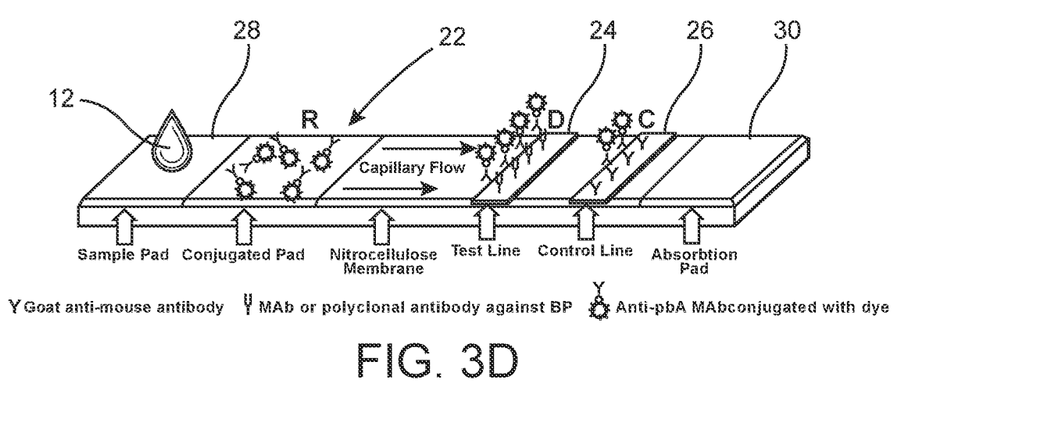
FIG. 3D is a schematic representation of the detection member of FIGS. 3A-3C representing operative features of each of a plurality of detection zones in the detection of at least one specific analyte.

Moreover, FIG. 3B provides a schematic representation of the operative mechanics of the detection zone 24. FIG. 3C provides a schematic representation of the operative mechanics of the control zone 26. FIG. 3D provides a summary of the operative mechanics of each of the plurality of detection zones 22, 24 and 26 with regard to a diagnostic procedure associated with a specific infectious agent, Bordetella Pertussis (BP) Toxin more specifically described hereinafter.

For purposes of clarity FIGS. 3A and 3D both contain explanatory and/or informational legends relating to the displayed icons, each icon representing a different reagent initially associated with different ones of the plurality of detection zones.

Accordingly, the reaction zone (R) 22 includes components, represented by the indicated icons, comprising analyte, analyte specific anti-body-chromophore conjugate, and control conjugate. As such, the reaction zone (R) 22 contains the analyte specific anti-body-chromophore conjugate that binds to, by way of example, a pathogen or protein associated with or excreted by a pathogen associated with at least one analyte. The analyte specific conjugate is soluble i.e. it will dissolve in the nasal aspirate, waste solution/biological sample and move with the liquid flow, via capillary action, and bind to the specific analyte in the reaction zone 22, if present. As indicated, the reaction zone 22 also contains a control conjugate that generates a positive signal in the control zone 26, if the control zone 26 is included in or as part of the detection member 20, as discussed in more detail hereinafter.

The detection zone (D) 24 is a zone of porous material that contains reagents also represented by the indicated icon, including an immobilized anti-body that binds and immobilizes the at least one analyte, including an associated pathogen or protein associated with or excreted by a pathogen. Since the at least one analyte passed through the reaction zone 22 prior to reaching the detection zone 24, the at least one analyte will be "tagged" with an analyte specific conjugate that results in the accumulation of the conjugated chromophore on the detection zone 24.

The control zone 26, if included, is a zone or section of the porous material detection member 20 that contains an immobilized anti-body, also identified by the indicated icon, that binds and immobilizes a control analyte such as for example protein conjugate that is totally unrelated to any of the protein matter that can be found in the nasal cavity or in the waste solution/biological sample emanating therefrom. The capture of the control conjugate results in the accumulation of the conjugated chromophore on a detection zone, which may provide an indication signal, alarm, etc. that the nasal irrigating diagnostic assembly 10, including the detection member 20, is operating correctly.

As practically applied, an analyte in the biological sample 12, for example a specific pathogen or a pathogen specific protein, binds to the soluble analyte specific conjugate. The analyte-conjugate complex continues to flow through the detection member and passes by a second, immobilized antibody that also binds to the at least one analyte thereby immobilizing the analyte-conjugate complex at a specific location on the detection member 20 the aforementioned corresponding to a detection zone. As indicated above, such a detection zone may be directly associated with the control zone 26 or detection zone 24 and may be viewable or otherwise detectable such as by appearance in an indicator window or like structure 50 associated with the nasal irrigation device 14, as represented in FIGS. 1 and 2. Since all analyte-conjugate complexes are concentrated in the detection zone 24, a line of the chromophore becomes visible at the detection zone 24 and within the indicator window 50. Otherwise, the analyte specific conjugate without the at least one analyte would pass the detection zone 24 and the detection line undetected. Macroscopically, if an analyte is present, the diagnostic member 20 changes colors in the window 50, as at indication line(s) 50', visible to the user. This provides an indication as to whether a specific analyte is identified in the waste solution/biological sample 12.

Further, a positive control signal will be generated by the control zone 26 to verify that the sample conditions do not interfere with antigen-anti-body interaction. The positive control signal is generated by an anti-body-chromophore conjugate or a protein-chromophore conjugate, represented by the indicated icon also embedded in detection member 20 together with the analyte specific conjugate in the reaction zone 22. The control conjugate migrates together with the nasal aspirate/waste fluid/biological sample 12 and is captured by an immobilized antibody located in the control zone 26, as represented, resulting in the generation of a visible signal.

Accordingly, in at least one preferred embodiment the detection member 20 comprises a bio-sensing strip or other appropriate configuration formed from a paper-based material which may be porous and which is capable of capillary flow or other structure which facilitates fluid flow through the detection member 20, for successive disposition relative to the plurality of detection zones 22, 24 and 26. In addition it could be ink-jet printed material that deposits an enzyme or a number and colorimetric reagents onto the paper-based detection member. Color change indicating a control signal could be achieved by target recognition's, such as when the detection member contacts the microbe or toxin of interest, by the detection member 20, converting enzyme, anti-body or after number-based recognition to a measurable, visual preferably color signal 50'. Other readout mechanisms could be incorporated, such as fluorescence and ultraviolet light. However, these latter alternatives may involve the inclusion of additional readers, equipment, detectors.

It is emphasized that one preferred embodiment of the present invention comprises disposing an ink-jet printed sol-gel material that deposits an enzyme, DNAzyme, or aptamer and colorimetric reagents onto the detection member or bio-sensing strip 20. As a result, color changes could be achieved and be apparent, upon target recognition. As used herein and as should be apparent, "target recognition" comprises or occurs when the paper-based strip 20 contacts the microbe or toxin of interest and by converting the enzyme, antibody or aptamer-based recognition to a measurable color signal. It is recognized that other readout mechanisms could be used such as, but not limited to, fluorescence and ultraviolet light. However, one potential disadvantage associated with these latter readout mechanisms is the possible requirement for an additional reader or piece of equipment needed and/or used to detect such additional or other readout mechanisms.

By way of example and with primary reference to FIG. 3D a diagnostic application or procedure, to detect a specific infectious agent Bordetella Pertussis Toxin (BP) or Pertussis Toxin (PT), the reaction zone 22 contains anti-BP antibodies capable of recognizing a single molecule moiety of epitope on BP associated molecules, such as filamentous hemagglutinin or PT. Examples of monoclonal antibodies against BP include: monoclonal antibody MApb 2A12, which binds to amino acids 399/623 or 781/828 of Adenylate Cyclase Toxin (ACT) excreted by BP and anti-PT antibody, which binds to PT subunit 1. The anti-BP monoclonal anti-bodies are conjugated with chromophores as labels to generate a signal such as color change in the detection zone 24 capable of being detected in window 50.

As with the monoclonal antibody essay represented in the figures, detection of the Bp or PT in a nasal wash or waste fluid sample can be achieved by replacing the conjugated pad with deposited enzymes, DNAzymes or aptamers specific for BP or PT along with colorimetric reagents. Methods for preparing various particles and immobilizing enzymes, DNAzymes, aptamers and colorimetric reagents on the detection strip 20 will be determined.

Therefore, structural and operative features of the nasal irrigation detection assembly 10 of the present invention provides a consumer or user with a handheld diagnostic device for detecting the presence of bacterial or viral pathogens, with no need for the participation of other medical personnel. Further, the detection procedure attendant with the nasal irrigation diagnostic assembly 10 provides results that are easy to read on a timely basis. In addition, the nasal irrigation device is combined with the diagnostic or detection member 20 and provides a continuous rinse with clean washing or cleaning liquid while draining the "contaminated" waste solution for retention and collection within the collection portion of the nasal irrigation device 14. Operation of the present invention thereby provides a device that has the potential to sample a broader surface area of the nasopharynx compared to a manual swab or an aspiration catheter as is conventionally used in the medical profession for related diagnostic procedures.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A nasal irrigation diagnostic assembly comprising:

an irrigation device including a housing having a first chamber section structured to removably contain irrigating fluid therein and a second chamber section, an applicator connected to said housing and dimensioned and configured to be inserted in the nasal cavity, said applicator comprising a first passage and a second passage, said first passage at least partially defining a flow path of irrigating fluid from said first chamber section into the nasal cavity, said second passage at least partially defining a path of travel of a drained waste solution from the nasal cavity into said second chamber section, said second chamber section further defining a fluid collection portion disposed and structured to retain a biological sample in the form of waste solution, from the nasal cavity, resulting from irrigation, said fluid collection portion disposed and structured to retain a biological sample, in the form of waste solution from the nasal cavity resulting from irrigation, a detection member, structured to determine the existence of at least one analyte biological sample of the waste solution, disposed in an operative position on said irrigation device in exposed relation to the biological sample, said detection member comprising a plurality of zones individually structured to analyze the biological sample upon engagement of said detection member with the biological sample, said plurality of zones include at least a reaction zone and a detection zone relatively disposed in successive fluid engagement with the waste solution and the biological sample, said reaction zone and said detection zone respectively include reagents cooperatively formulated and reactive to detect the existence of the at least one analyte, comprising a pathogen/pathogen specific protein, in the biological sample of the waste solution, said reaction zone including an analyte specific antibody-chromophore conjugate soluble in the waste solution; said analyte specific antibody-chromophore conjugate is configured to bind with the at least one analyte, said detection zone includes a first immobilized antibody configured to bind with and immobilize the at least one analyte, said plurality of zones further comprises a control zone, said control zone configured to provide an indication of valid operation of at least said detection member, said detection member further comprising a sample pad disposed in fluid communicating relation to said plurality of zones, said operative position comprising at least said sample pad disposed within said fluid collection, in direct engagement with the waste solution from the nasal cavity collected within the fluid collection portion, and said detection member comprises a paper-based material having a porous construction structured to facilitate capillary flow of the waste solution from the sample pad to each of the plurality of zones.

2. The nasal irrigation diagnostic assembly as recited in claim 1 wherein said control zone includes a second immobilized antibody configured to bind with and immobilize said at least one analyte.

3. The nasal irrigation diagnostic assembly as recited in claim 1 further comprising said detection member including a sol-gel material disposed thereon, said sol-gel material configured for depositing an enzyme, DNAzyme or aptamer and at least one colorimetric agent on said detection member.

4. The nasal irrigation diagnostic assembly as recited in claim 3 wherein said sol-gel material is disposed on said detection member via an ink-jet procedure.

5. The nasal irrigation diagnostic assembly as recited in claim 3 wherein said at least one colorimetric agent is formulated to generate a color change upon target recognition.

6. The nasal irrigation diagnostic assembly as recited in claim 5 wherein said target recognition comprises contact of said detection member with a targeted microbe or toxin.

7. The nasal irrigation diagnostic assembly as recited in claim 6 wherein said enzyme, DNAzyme or aptamer are specific for Bp or PT.

* * * * *